United States Patent
Fujiwhara et al.

[11] 3,973,968
[45] Aug. 10, 1976

[54] PHOTOGRAPHIC ACYL ACETANILIDE COLOR COUPLERS WITH 2,5-DIOXO-1-IMIDAZOLIDINYL COUPLING OFF GROUPS

[75] Inventors: Mitsuto Fujiwhara, Hachioji; Syunji Matsuo, Fussa; Tamotsu Kojima, Kokubunji, all of Japan

[73] Assignee: Konishiroku Photo Industry Co., Ltd., Tokyo, Japan

[22] Filed: Apr. 6, 1972

[21] Appl. No.: 241,691

[30] Foreign Application Priority Data
Apr. 26, 1971  Japan................. 46-26766

[52] U.S. Cl.................. 96/56.5; 96/100
[51] Int. Cl.[2]............ G03C 7/00; G03C 1/40
[58] Field of Search............. 96/100, 56.2, 56.5

[56] References Cited
UNITED STATES PATENTS

| | | | |
|---|---|---|---|
| 2,632,702 | 3/1953 | Sawdey............... | 96/56.5 |
| 3,328,419 | 6/1967 | Anderson............. | 96/100 |
| 3,458,315 | 7/1969 | Loria................. | 96/56.2 |
| 3,730,722 | 5/1973 | Inoue et al.......... | 96/100 |

*Primary Examiner*—David Klein
*Assistant Examiner*—R. L. Schilling
*Attorney, Agent, or Firm*—Bierman & Bierman

[57] ABSTRACT

An imagewise-exposed, light-sensitive silver halide color photographic material is developed, by use of developer, in the presence of a compound of the general formula:

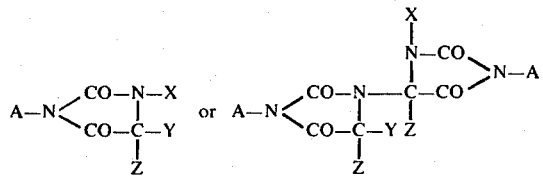

wherein A is a residue formed by removing one of the hydrogen atoms of the active methylene group of an active methylene group-containing yellow image-forming coupler of the acyl acetanilide type; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl, or anilino group.

8 Claims, 1 Drawing Figure

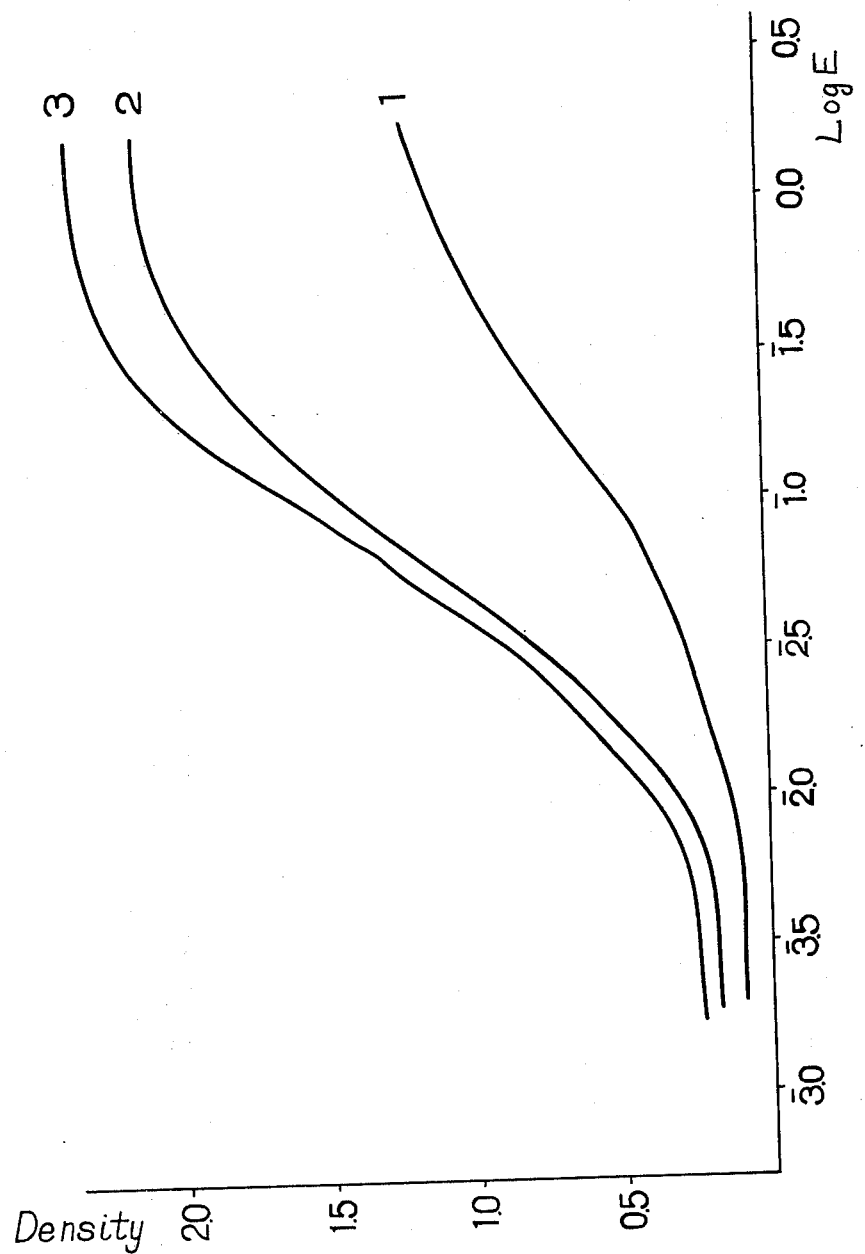

PHOTOGRAPHIC ACYL ACETANILIDE COLOR COUPLERS WITH 2,5-DIOXO-1-IMIDAZOLIDINYL COUPLING OFF GROUPS

This invention relates to a process for forming yellow images of light-sensitive color photographic materials. More particularly, the present invention pertains to a process for forming yellow dye images of light-sensitive color photographic materials using novel 2-equivalent yellow dye image-forming couplers.

A photographic process for forming a dye image by exposing a photographic material containing couplers and then developing the exposed photographic material with a developer containing an aromatic primary amine type developing agent as active ingredient has already been well known. Among the couplers used in the above-mentioned process, the yellow coupler has an active methylene group which is useful for forming a yellow dye by coupling with an oxidation product of the aromatic amine type developing agent. In case this active methylene has not been substituted, 4 molecules of silver halide is required in order to form 1 molecule of the dye at the time of development. Accordingly, the said coupler is called as a 4-equivalent coupler. It is also well known, however, that the same dye as in the case of the above-mentioned coupler having the said active methylene can be formed from a coupler, in which one of the hydrogen atoms of the active methylene contained therein has been substituted by a halogen atom such as chloride atom. In this case, the halogen atom is released during the color development reaction and 2 molecules of developed silver halide can form 1 molecule of a dye, so that the said coupler is called as a 2-equivalent coupler. The 2-equivalent coupler has such advantages as mentioned below over the 4-equivalent coupler.

1. The coupling rate is more enhanced than in the case of the conventional 4-equivalent coupler.
2. The amount of silver halide may be decreased to one half of the amount required for formation of the same dye as in the case of the 4-equivalent coupler, so that the production cost of photographic material can be reduced.
3. The emulsion layer can be made thinner, and the color image obtained is improved in resolution and sharpness.
4. In the case of a multi-layered photographic material, the permeation of light into the lower layers is improved to provide an excellent photographic speed.

Due to the above-mentioned advantages, the use of the 2-equivalent coupler makes it extremely successful to form a color image in a multi-layered color photographic material.

Such 2-equivalent coupler as mentioned above is a yellow image-forming coupler containing an active methylene, one of the hydrogen atoms of which has been substituted, and the substituent contained in said active methylene has the property that it is liberated at the time of color development.

A certain 2-equivalent coupler tends to form color stains such as fog and the like and has a property of disturbing the developability of a photographic material containing said coupler. However, the 2-equivalent coupler used in the present invention is not only colorless but also high in reactivity and scarcely forms stains. Further, a yellow dye formed at the time of color development from the yellow coupler used in the present invention is excellent in fastness to light, humidity and heat, has no unnecessary absorption in the long wavelength region, is less in absorption at the green light area, shows sharp absorptions, and provides an extremely favorable hue at the time of color reproduction.

The coupler used in the present invention is a 2-equivalent coupler of the following general formula:

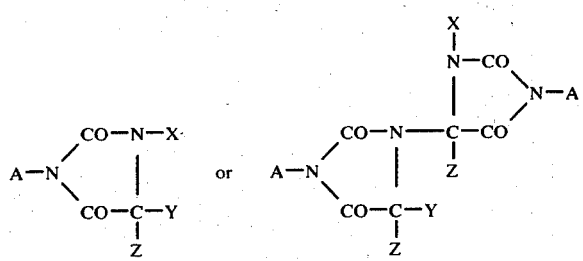

wherein A is a residue formed by removing one of the hydrogen atoms of the active methylene group contained in the coupler; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl or anilino group.

Typical examples of the substituent of the coupler used in the present invention are as follows:

2,5-Dioxo-1-imidazolidinyl
3-Methyl-2,5-dioxo-1-imidazodinyl
3-Ethyl-2,5-dioxo-1-imidazodinyl
3-Propyl-2,5-dioxo-1-imidazolidinyl
3-Isopropyl-2,5-dioxo-1-imidazolidinyl
3-Phenyl-2,5-dioxo-1-imidazolidinyl
3-(p-Chlorophenyl)-2,5-dioxo-1-imidazolidinyl
3-(o-Tolyl)-2,5-dioxo-1-imidazolidinyl
3-(m-Tolyl)-2,5-dioxo-1-imidazolidinyl
3-(p-Tolyl)-2,5-dioxo-1-imidazolidinyl
3-(4-Bromo-m-tolyl)-2,5-dioxo-1-imidazolidinyl
3-(2,4-Xylyl)-2,5-dioxo-1-imidazolidinyl
3-Mesityl-2,5-dioxo-1-imidazolidinyl
3-(p-Methoxyphenyl)-2,5-dioxo-1-imidazolidinyl
3-(p-Ethoxyphenyl)-2,5-dioxo-1-imidazolidinyl
3-(2-Bromo-4-ethoxyphenyl)-2,5-dioxo-1-imidazolidinyl
3-Acetyl-2,5-dioxo-1-imidazolidinyl
3-Carboxymethyl-2,5-dioxo-1-imidazolidinyl
3-Methoxycarbonylmethyl-2,5-dioxo-1-imidazolidinyl
3-Ethoxycarbonylmethyl-2,5-dioxo-1-imidazolidinyl
3-Carbamylmethyl-2,5-dioxo-1-imidazolidinyl
4-Methyl-2,5-dioxo-1-imidazolidinyl
3,4-Dimethyl-2,5-dioxo-1-imidazolidinyl
3,4-Diethyl-4-methyl-2,5-dioxo-1-imidazolidinyl
4-Ethyl-2,5-dioxo-1-imidazolidinyl
3-Ethyl-4-methyl-2,5-dioxo-1-imidazolidinyl
3-(o-Tolyl)-4-ethyl-2,5-dioxo-1-imidazolidinyl
3-Acetyl-4-methyl-2,5-dioxo-1-imidazolidinyl
4,4-Dimethyl-2,5-dioxo-1-imidazolidinyl
3,4,4-Trimethyl-2,5-dioxo-1-imidazolidinyl
3-Naphthyl-4,4-dimethyl-2,5-dioxo-1-imidazolidinyl
4,4-Diethyl-2,5-dioxo-1-imidazolidinyl
4-Phenyl-2,5-dioxo-1-imidazolidinyl
4-(p-Chlorophenyl)-2,5-dioxo-1-imidazolidinyl
3-Methyl-4-phenyl-2,5-dioxo-1-imidazolidinyl
3-Benzyl-2,5-dioxo-1-imidazolidinyl 3-(p-Methylbenzyl)-2,5-dioxo-1-imidazolidinyl
3-Benzyl-4-methyl-2,5-dioxo-1-imidazolidinyl
4-Benzyl-2,5-dioxo-1-imidazolidinyl
4-Phenethyl-2,5-dioxo-1-imidazolidinyl
4,4-Diphenyl-2,5-dioxo-1-imidazolidinyl
4-Ureido-2,5-dioxo-1-imidazolidinyl
3-Methyl-4-ureido-2,5-dioxo-1-imidazolidinyl
3-Nitro-2,5-dioxo-1-imidazolidinyl
3-Amino-2,5-dioxo-1-imidazolidinyl
3-Nitro-4-methyl-2,5-dioxo-1-imidazolidinyl
4-Benzylidene-2,5-dioxo-1-imidazolidinyl
4-Styryl-2,5-dioxo-1-imidazolidinyl
4-Anilino-4-phenyl-2,5-dioxo-1-imidazolidinyl
2,4,2',4'-Tetraoxo-1,5'-biimidazolidine-3,3'-diyl.

Typical examples of the coupler used in the present invention are shown below, but couplers usable in the invention are not limited to these.

Exemplified couplers:

1. α-(2,5-Dioxo-1-imidazolidinyl)-α-pivalyl-acetanilide

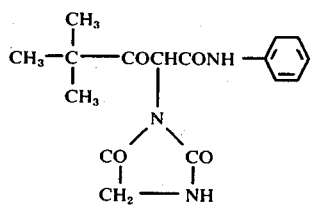

m.p. 230° – 233°C

2. α-(2,5-Dioxo-1-imidazolidinyl)-α-(p-octadecyloxybenzoyl)-2-methoxy-acetanilide

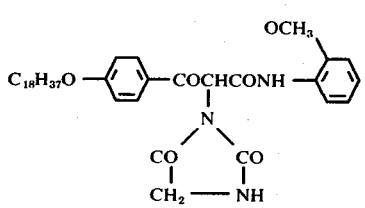

m.p. 155° – 157°C

3. α-(2,5-Dioxo-1-imidazolidinyl)-α-pivalyl-2-chloro-5-φ-(2,4-di-t-amylphenoxy)-butyramido-acetanilide

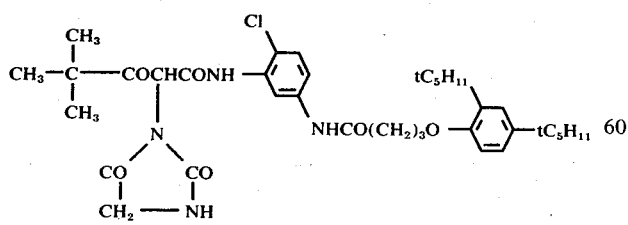

m.p. 184° – 187°C

4. α-[3-(2-Ethylhexyl)-2,5-dioxo-1-imidazolidinyl]-α-pivalyl-2,5-dichloroacetanilide

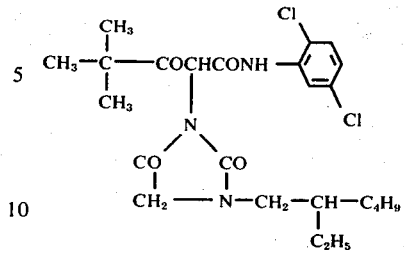

m.p. 28° – 30°C

5. α-(3-Phenyl-2,5-dioxo-1-imidazolidinyl)-α- 3-[α-(2,4-di-t-amylphenoxy)butyramido]-benzoyl -2-methoxyacetanilide

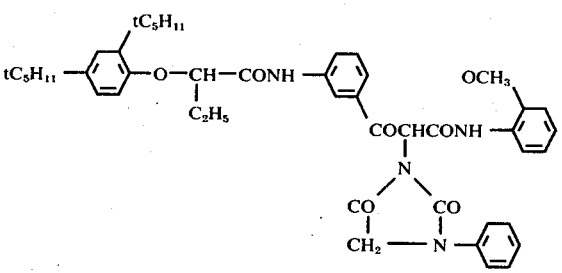

m.p. 110° – 115°C

6. α-(3-Phenyl-2,5-dioxo-1-imidazolidinyl)-α-pivalyl-2-chloro-5-[φ-(2,4-di-t-amylphenoxy)-butyramido]-acetanilide

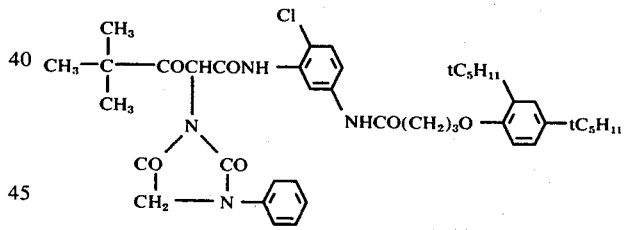

m.p. 182° – 185°C

7. α-(3-Benzyl-2,5-dioxo-1-imidazolidinyl)-α-pivalyl-acetanilide

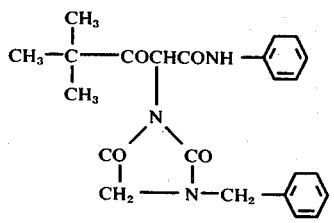

m.p. 165° – 167°C

8. α-(3-Methyl-2,5-dioxo-1-imidazolidinyl)-α-pivalyl-acetanilide

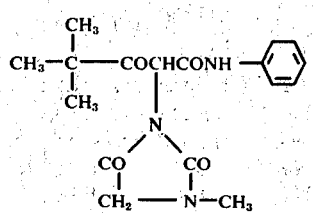

m.p. 202° – 204°C

9. α-(3-Acetyl-2,5-dioxo-1-imidazolidinyl)-α-benzoyl-2-chloro-5-[1-(n-dodecyloxycarbonyl) ethoxycarbonyl]-acetanilide

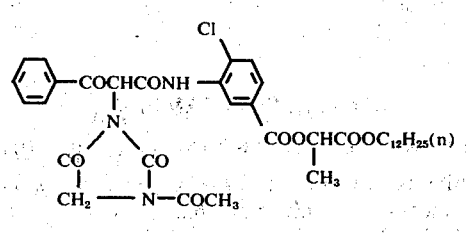

m.p. 45° – 50°C

10. α-[3-(p-Chlorophenyl)-4,4-dimethyl-2,5-dioxo-1-imidazolidinyl]-α-pivalyl-2,5-dichloroacetanilide

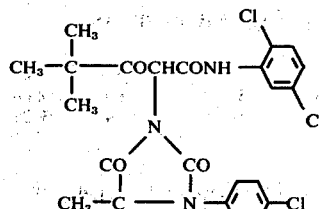

m.p. 214° – 216°C

11. α-[4-(p-Methylbenzyl)-2,5-dioxo-1-imidazolidinyl]-α-(p-octadecyloxybenzoyl)-3,5-dicarboxyacetanilide dipotassium salt

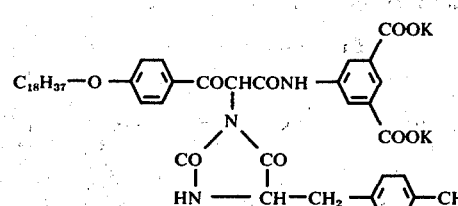

m.p. Above 270°C

12. α-[3-(p-Ethoxyphenyl)-4-phenyl-2,5-dioxo-1-imidazolidinyl]-α-pivalyl-acetanilide

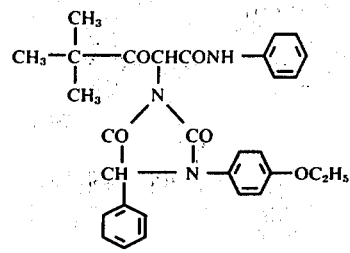

m.p. 220° – 222°C

13. α,α'-(2,4,2',4'-Tetraoxo-1,5'-biimidazolidine-3,3'-diyl)-bis-(α-pivalyl-2,5-dichloroacetanilide)

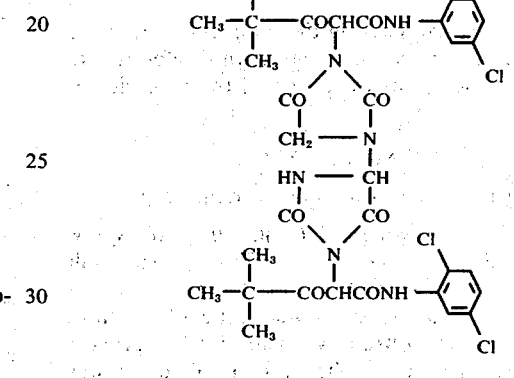

m.p. 105° – 108°C

14. α-(4-Ureido-2,5-dioxo-1-imidazolidinyl)-α-pivalyl-acetanilide

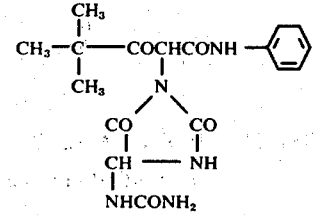

m.p. 166° – 169°C

15. α-(3-Methyl-2,5-dioxo-1-imidazolidinyl)-α-pivalyl-2-chloro-5-[γ-(2,4-di-t-amylphenoxy)-butyramido]-acetanilide

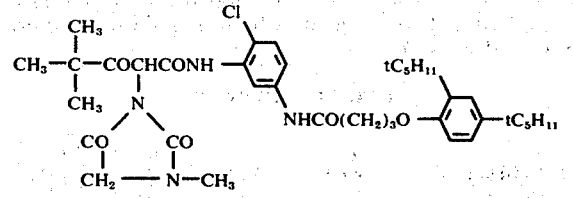

m.p. 126° – 128°C

16. α-(4-Methyl-3-ethoxycarbonylmethyl-2,5-dioxo-1-imidazolidinyl)-α-(o-methoxybenzoyl)-3,5-dicarboxyacetanilide dipotassium salt

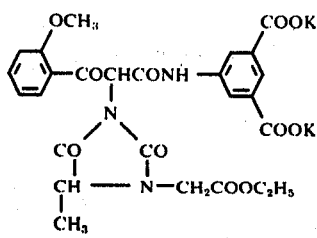

m.p. Above 270°C

The above-mentioned compounds can be synthesized by reacting a yellow image-forming coupler having an active methylene group, in which one of the hydrogen atoms of the active methylene group which are bonded to two carbonyl groups has been substituted by a halogen atoms, with a substituted or unsubstituted hydantoin or bihydantoin.

Procedures for synthesizing the couplers used in the present invention are set forth below with reference to Synthesis Examples, but the scope of the invention is not limited thereto.

SYNTHESIS EXAMPLE 1

Synthesis of the exemplified coupler (1)

A mixture comprising 12.6 g. of α-pivalyl-α-chloroacetanilide and 10 g. of hydantoin potassium salt was reacted under reflux for 6 hours in 200 ml. of acetonitrile. Thereafter, the liquid reaction mixture was filtered, and the filtrate was vaporized to dryness under reduced pressure. The residue obtained was recrystallized from a mixed solvent comprising n-hexane and alcohol to obtain 6 g. of white crystalline needles, m.p. 230° – 233°C.

Elementary analysis:

|  | C | H | N |
|---|---|---|---|
| Calculated (%) | 60.55 | 6.03 | 13.24 |
| Found (%) | 60.62 | 5.86 | 13.53 |

SYNTHESIS EXAMPLE 2

Synthesis of the exemplified coupler (3)

A mixture comprising 25 g. of α-pivalyl-α-chloro-2-chloro-5-[γ-(2,4-di-t-amylphenoxy)butyramido]-acetanilide and 8 g. of hydantoin potassium salt was reacted under reflux for 2 hours in 250 ml. of acetonitrile. Thereafter, the liquid reaction mixture was filtered, and the filtrate was vaporized to dryness under reduced pressure. The residue obtained was recrystallized from a mixed solvent comprising n-hexane and alcohol to obtain 15 g. of white crystalline powder, m.p. 184° – 187°C.

Elementary analysis:

|  | C | H | N | Cl |
|---|---|---|---|---|
| Calculated (%) | 64.60 | 7.38 | 8.37 | 5.92 |
| Found (%) | 64.57 | 7.42 | 8.34 | 5.00 |

SYNTHESIS EXAMPLE 3

Synthesis of the exemplified coupler (5)

A mixture comprising 22.3 g. of α-{3-[α-(2,4-di-t-amylphenoxy)butyramido]benzoyl}-α-bromo-2-methoxy-acetanilide and 10 g. of 1-phenylhydantoin potassium salt was reacted under reflux for 1 hour in 200 ml. of acetonitrile. Thereafter, the liquid reaction mixture was filtered, and the filtrate was vaporized to dryness under reduced pressure. The residue obtained was dissolved in 300 ml. of ethyl acetate, and the resulting solution was washed 2 times with 100 ml. of an aqueous 1N-NaOH solution, 1 time with 100 ml. of an aqueous 1N-HCl solution, and 3 times with 100 ml. of water. Subsequently, the ethyl acetate solution was vaporized to dryness under reduced pressure, and the residue was washed 3 times with 50 ml. of hot n-hexane to obtain 13 g. of a pale yellow powder, m.p. 110° – 115°C.

Elementary analysis:

|  | C | H | N |
|---|---|---|---|
| Calculated (%) | 71.02 | 6.88 | 7.36 |
| Found (%) | 71.03 | 7.15 | 7.09 |

SYNTHESIS EXAMPLE 4

Synthesis of the exemplified compound (10)

A mixture comprising 7.4 g. of α-pivalyl-α-bromo-2,5-dichloroacetanilide and 6.2 g. of 1-(p-chlorophenyl)-5,5-dimethylhydantoin and 4 g. of triethylamine was reacted under reflux for 4 hours in 150 ml. of acetonitrile. Thereafter, the liquid reaction mixture was vaporized to dryness, and the residue was charged with water and filtered to obtain crystals. The crystals were recrystallized from alcohol to obtain 4 g. of white crystalline mass, m.p. 214° – 216°C.

Elementary analysis:

|  | C | H | N | Cl |
|---|---|---|---|---|
| Calculated (%) | 54.92 | 4.60 | 8.06 | 20.26 |
| Found (%) | 54.90 | 4.74 | 8.21 | 20.29 |

SYNTHESIS EXAMPLE 5

Synthesis of the exemplified compound (13)

A mixture comprising 6.4 g. of α-chloro-α-pivalyl-2,5-dichloroacetanilide and 2.8 g. of 1,5'-bishydantoin dipotassium salt was reacted under reflux for 3 hours in 150 ml. of acetonitrile. Thereafter, the liquid reaction mixture was poured into 500 ml. of water, and deposited white crystals were recovered by filtration. The recovered crystals were recrystallized from a mixed solvent comprising n-hexane and ethanol to obtain 4 g. of a white powder, m.p. 105° – 108°C.

Elementary analysis:

|  | C | H | N | Cl |
|---|---|---|---|---|
| Calculated (%) | 49.88 | 4.18 | 10.90 | 18.40 |
| Found (%) | 49.61 | 4.30 | 11.12 | 18.27 |

A developing agent used for development in the present process for forming yellow images of light-sensitive color photographic materials is a phenylenediamine type silver halide-developing agent or a p-aminophenol type developing agent in which the amino group has not been substituted. Examples of the developing agent are as shown below.

Diethyl-p-phenylenediamine hydrochloride
Monomethyl-p-phenylenediamine hydrochloride Dimethyl-p-phenylenediamine hydrochloride
2-Amino-5-diethylaminotoluene hydrochloride
2-Amino-5-(N-ethyl-N-dodecylamino) toluene
N-Ethyl-N-β-methanesulfonamidoethyl-3-methyl-4-aminoaniline hydrochloride
N-Ethyl-N-β-methanesulfonamidoethyl-4-aminoaniline
4-N-Ethyl-N-β-hydroxyethylaminoaniline.

Some of the couplers used in the present invention are incorporated into an alkaline developer. The developer may contain a sulfite, carbonate, bisulfite, bromide, or iodide of an alkali metal.

An example of the composition of a typical developer containing the coupler which is used in the present invention is as follows:

| | |
|---|---|
| 2-Amino-5-diethylaminotoluene hydrochloride | 2.0 g. |
| Anhydrous sodium sulfite | 2.0 g. |
| Anhydrous sodium carbonate | 20.0 g. |
| Potassium bromide | 1.0 g. |
| Exemplified coupler (1) | 2.0 g. |
| Water to make | 1,000 ml. |

In order to incorporate the couplers used in the present invention into light-sensitive color photographic emulsions, any of the known procedures may be adopted. For example, there may be adopted the following procedure:

One or a mixture of the couplers is dissolved in either one or a mixture of a high boiling solvent having a boiling point of more than 175°C. such as tricresyl phosphate or dibutyl phthalate and a low boiling solvent such as ethyl acetate or butyl propionate. The resulting solution is mixed with an aqueous gelatin solution containing a surface active agent and then emulsified and dispersed by means of a high speed rotary mixer or a colloid mill. The thus obtained coupler dispersion is incorporated directly into a silver halide photographic emulsion, which is then coated on a support, followed by drying. Alternatively, the above-mentioned coupler dispersion is set, extruded to noodles, freed from the low boiling solvent by water-washing or the like means, and incorporated into a silver-halide photographic emulsion, which is then coated on a support, followed by drying. In this case, the amount of the coupler to be incorporated is preferably 10 to 300 g. per mole of the silver halide used, though the amount may be varied according to the application purpose of the resulting photographic material.

Among the 2-equivalent yellow dye image-forming couplers used in the present invention, the exemplified couplers (5), (6) and (9) can be dispersed into a photographic emulsion according to the above-mentioned procedure without using the high boiling solvent; the exemplified coupler (11) can be dispersed in a photographic emulsion according to the Fischer's dispersion method; the exemplified coupler (1) can be incorporated into a developer; and the exemplified coupler (4) can be used for diffusion transfer since it forms a diffusing dye.

For the preparation of photographic emulsions used in the present invention, various silver halides such as silver chloride, silver iodobromide, silver chlorobromide and the like may be used. Further, the emulsions may have been subjected to chemical sensitization or optical sensitization using a carbocyanine dye or merocyanine dye, and may contain ordinary photographic additives such as, for example, anti-foggant, stabilizer, anti-stain agent, anti-irradiation agent, high molecular additive, hardener, coating aid and the like.

A light-sensitive color photographic material containing the coupler used in the present invention may be incorporated with an ultraviolet absorber, whereby the resulting color image can further be enhanced in fastness. Further, the color developer may contain a development-controlling agent such as citrazinic acid or the like, in addition to the aforesaid developing agent.

The present invention is illustrated in further detail below with reference to examples, but the invention is not limited to these examples.

EXAMPLE 1

20.0 Grams of each of the exemplified couplers (3), (6) and (9) was completely dissolved at 60°C. in a mixed solvent comprising 20 ml. of dibutyl phthalate and 60 ml. of ethyl acetate. This solution was mixed with 10 ml. of a 6% aqueous solution of Alkanol B (alkylnaphthalenesulfonate produced by Du Pont) and 200 ml. of a 6% aqueous gelatin solution, and the mixed solution was emulsified and dispersed by means of a colloid mill to form a coupler dispersion.

The above-mentioned coupler dispersion was added to 1 kg. of a high speed silver iodobromide emulsion, which was then coated on a film base and dried to prepare a light-sensitive photographic material having a stable film. The photographic material was exposed according to an ordinary procedure, and then developed at 20°C. for 10 minutes with a developer of the following composition:

| | |
|---|---|
| N-Ethyl-N-β-methanesulfonamidoethyl-3-methyl-4-aminoaniline sulfate | 5.0 g. |
| Anhydrous sodium sulfite | 2.0 g. |
| Benzyl alcohol | 3.8 g. |
| Sodium carbonate (monohydrate) | 50.0 g. |
| Potassium bromide | 1.0 g. |
| Sodium hydroxide | 0.55 g. |
| Water to make | 1,000 ml. |

Subsequently, the developed photographic material was subjected to ordinary stopping, fixing and bleaching treatments.

The absorption maximum (λ-max), maximum density (D-max) and storability of each of the thus obtained color images were as set forth in Table 1, in which are also shown those of color images formed by using light-sensitive color photographic materials prepared in the same manner as above, except that the couplers used were identical in structure with those used in the above but had not been substituted in hydrogen atoms of active methylene groups.

Table 1

| | | Color image | | | |
|---|---|---|---|---|---|
| | | | | Ratio of residual dye | |
| Run No. | Coupler | G2--max (mμ) | D-max | Light fastness | Humidity fastness |
| 1 | Control | 447 | 1.22 | 96 | 99 |
| 2 | Exemplified coupler (3) | 447 | 2.40 | 96 | 99 |
| 3 | Control | 447 | 1.23 | 95 | 99 |
| 4 | Exemplified coupler (6) | 447 | 2.12 | 97 | 100 |
| 5 | Control | 452 | 1.90 | 75 | 100 |
| 6 | Exemplified coupler (9) | 453 | 2.40 | 78 | 100 |

Control: Active point-unsubstituted type coupler identical in structure with the exemplified coupler.

Table 1-continued

| Run No. | Coupler | G2--max (mμ) | D-max | Color image Light fastness | Ratio of residual dye Humidity fastness |
|---|---|---|---|---|---|

λ-max and D-max: Calculated by measuring the spectral absorption and density of each color image.
Ratio of residual dye: Ratio (%) of residual dye after treating each color image at a portion where the initial density was 1.0.
Treatment conditions:
    Light fastness: Xenon arc lamp, 50°C. 30 hrs.
    Humidity fastness: 50°C. 80% RH, 7 days.

As shown in Table 1, the couplers of the present invention display favorable characteristics and are usable in multi-layered and multicolor photographic materials.

EXAMPLE 2

In the same manner as in Example 1, each of the exemplified couplers (6) and (15) was dispersed in a gelatin-silver iodobromide emulsion. The amount of the silver halide used was the same as in Example 1. Subsequently, the emulsion was treated in the same manner as in Example 1 to prepare a light-sensitive photographic material containing each of the exemplified couplers (6) and (15).

For comparison, a control photographic material was prepared in the same manner as above, except that the coupler used was a coupler not substituted at an active methylene group but identical in other structure with the coupler of the present invention which is a 4-equivalent coupler.

Each of the thus prepared photographic materials was exposed and then developed with the same developer as in Example 1.

The density of yellow dye formed at each stage by exposing each photographic material to blue light was measured by means of a densitometer and shown in the accompanying drawing, in which the horizontal axis represents the amount of exposure (log E) and the vertical axis represents the density. In the drawing, the curve 1 shows the case of the control photographic material containing the 4-equivalent coupler, and the curves 2 and 3 show the cases of the photographic materials containing the exemplified couplers (6) and (15), respectively. The amount of silver halide contained in each of the photographic materials according to the present invention was identical with that of the control photographic material. As is clear from the drawing, the 2-equivalent couplers of the present invention are sufficiently usable even when the amount of silver is reduced to one half of the amount used hitherto.

1. Unsubstituted type coupler identical in other structure with the coupler of the present invention.
2. Exemplified coupler (6).
3. Exemplified coupler (15).

EXAMPLE 3

The exemplified coupler (11) was dispersed in a mixed solvent comprising ethanol and water, and then dissolved by addition of a 10% caustic soda solution. This solution was mixed with an aqueous gelatin solution containing 12% of gelatin and 5.13 g. of Alkanol B, and the mixed solution was neutralized with acetic acid. Subsequently, the solution was dispersed in a silver halide emulsion containing silver iodobromide, and the emulsion was coated on a support and then dried to prepare a photographic material. The thus prepared photographic material was exposed according to an ordinary procedure, and then treated in the same manner as in Example 1.

The photographic properties of the resulting color image were as set forth in Table 2, in which are also shown the photographic properties of a color image obtained by use of a control photographic material prepared in the same manner as above, except that the coupler used was an unsubstituted type coupler identical in other structure with the coupler of the present invention.

Table 2

| Coupler | Fog | λ-max | D-max |
|---|---|---|---|
| Exemplified coupler (11) | 0.12 | 450 | 2.06 |
| Unsubstituted type coupler | 0.10 | 450 | 1.85 |

As is clear from Table 2, the coupler of the present invention shows favorable results even when used according to the Fischer's dispersion method.

EXAMPLE 4

A photographic emulsion containing the exemplified coupler (4) was coated on a support and then dried to prepare a light-sensitive photographic material. This photographic material was exposed and then treated with an alkaline developer (pH 13) containing 2 g/l of $Na_2SO_3$ and 11 g/l of 4-N-ethyl-N-$\beta$-hydroxyethyl aminoaniline. The resulting negative was brought into close contact at 24°C. for 3 minutes with an image-receiving sheet containing dimethyl-$\beta$-hydroxyethyl-$\gamma$-stearamidopropylammonium dihydrogen phosphate (mordant). Thereafter, the image-receiving sheet was peeled off, whereby the yellow dye formed had transferred to the image-receiving sheet to give an excellent positive image.

EXAMPLE 5

An ordinary silver iodobromide emulsion was coated on a support and then dried to prepare a light-sensitive material. This photographic material was subjected to an ordinary external development using the exemplified coupler (1)-containing developer mentioned previously.

The photographic properties of the resulting color image were as set forth in Table 3, in which are also shown the photographic properties of a color image obtained by treating the photographic material with an external developer containing an unsubstituted type coupler identical in other structure with the coupler of the present invention.

Table 3

| Coupler | Fog | λ-max | D-max |
|---|---|---|---|
| Exemplified coupler (1) | 0.05 | 442 | 2.01 |
| Unsubstituted type coupler | 0.04 | 443 | 1.47 |

What is claimed is:

1. A process for forming yellow-dye image of light-sensitive color photographic materials, characterized in developing an imagewise-exposed, light-sensitive silver halide color photographic material, by use of a developer, in the presence of at least one compound of the general formula:

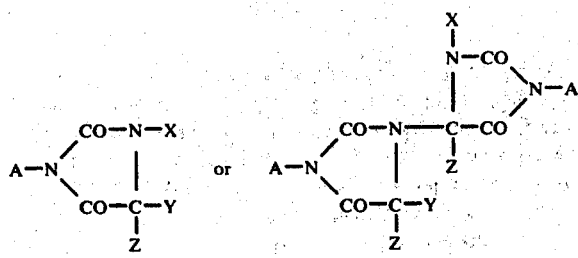

wherein A is a residue formed by removing one of the hydrogen atoms of the active methylene group of an active methylene group-containing yellow image-forming coupler of the acyl acetanilide type; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl or anilino group.

2. A process for forming yellow-dye images of light-sensitive color photographic materials as claimed in claim 1, wherein said compound is at least one member selected from the group consisting of α-(2,5-dioxo-1-imidazolidinyl)-α-pivalyl-acetanilide, α-(2,5-dioxo-1-imidazolidinyl)-α-(p-octadecyloxybenzoyl)-2-methoxyacetanilide, α-(2,5-dioxo-1-imidazolidinyl)-α-pivalyl-2-chloro-5γ(2,4-di-t-amylphenoxy)-butyramidoacetanilide, α-[3-(2-ethylhexyl)-2,5-dioxo-1-imidazolidinyl]-α-pivalyl-2,5-dichloroacetanilide, α-(3-phenyl-2,5-dioxo-1-imidazolidinyl)-α{3-(2,4-di-t-amylphenoxy)butyramido]-benzoyl}-2-methoxyacetanilide, α-(3-phenyl-2,5-dioxo-1-imidazolidinyl)-α-pivalyl-2-chloro-5-[γ-(2,4-di-t-amylphenoxy)-butyramidoacetanilide, α-(3-benzyl-2,5-dioxo-1-imidazolidinyl)-α-pivalyl-acetanilide, α-(3-methyl-2,5-dioxo-1-imidazolidinyl)-α-pivalyl-acetanilide, α-(3-acetyl-2,5-dioxo-1-imidazolidinyl)-α-benzolyl-2-chloro-5-[1-(n-dodecyloxycarbonyl)ethoxycarbonyl]-acetanilide, α-[3-p-chlorophenyl)-4,4-dimethyl-2,5-dioxo-1-imidazolidinyl]-α-pivalyl-2,5-dichloroacetanilide, α-[4-(p-methylbenzyl)-2,5-dioxo-1-imidazolidinyl]-α-(p-octadecyloxybenzoyl)-3,5-dicarboxyacetanilide dipotassium salt, α-[3-(p-ethoxyphenyl)-4-phehyl-2,5-dioxo-1-imidazolidinyl]-α-pivalyl-acetanilide, α,α'-(2,4,2',4'-tetraoxo-1,5'-biimidazolidine-3,3'-diyl)-bis-(α-pivalyl-2,5-dichloroacetanilide), α-(4-ureido-2,5-dioxo-1-imidazolidinyl)-α-pivalyl-acetanilide, α-(3-methyl-2,5-dioxo-1-imidazolidinyl)-α-pivalyl-2-chloro-5-[γ-(2,4-di-t-amylphenoxy)-butylamido]-acetanilide and α-(4-methyl-3-ethoxycarbonylmethyl-2,5-dioxo-1-imidazolidinyl)-α-(o-methoxybenzoyl)-3,5-dicarboxyacetanilide dipotassium salt.

3. A light-sensitive silver halide color photographic material which comprises a support and carried thereon an yellow color image-forming layer comprising a compound of the general formula

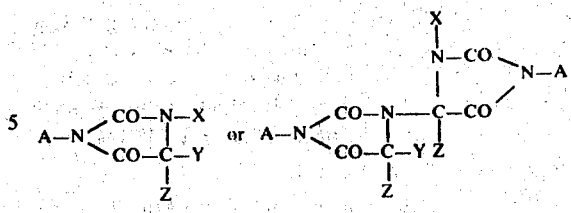

wherein A is a residue formed by removing one of the hydrogen atoms of the active methylene group of an active methylene group-containing yellow image-forming coupler of the acyl acetanilide type; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl or anilino group.

4. A developer for light-sensitive silver halide color photographic materials which comprises a p-phenylenediamine type developing agent and a compound of the general formula

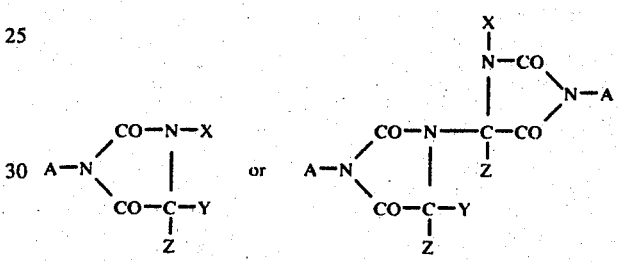

wherein A is a residue formed by removing one of the hydrogen atoms of the active methylene group of an active methylene group-containing yellow image-forming coupler of the acyl acetanilide type; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl or anilino group.

5. A process for forming yellow-dye image of light-sensitive color photographic materials according to claim 1, wherein said compound is incorporated into the light-sensitive color photographic material.

6. A process for forming yellow-dye image of light-sensitive color photographic materials according to claim 1, wherein said compound is incorporated into the developer.

7. A method for forming dye images comprising processing an exposed silver halide photographic emulsion with an aqueous alkaline solution containing an aromatic primary amine developing agent in the presence of a yellow forming coupler having the following general formula

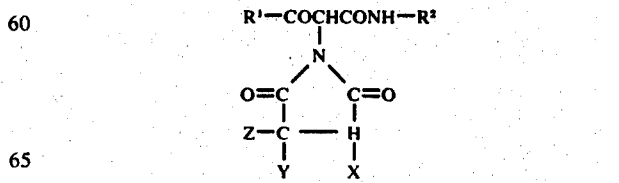

wherein $R_1$ is tertiary butyl; $R_2$ is an aryl group; X is a hydrogen atom, or an alkyl, acyl, carboxymethyl, alkoxycarbonylmethyl, carbamylmethyl, aryl, aralkyl, nitro or amino group; and Y and Z are individually a hydrogen atom, or an alkyl, ureido, aryl, aralkyl, benzylidene, styryl or anilino group.

8. A method for forming dye images comprising processing an exposed silver halide photographic emulsion with an aqueous alkaline solution containing an aromatic primary amino developing agent in the presence of a yellow forming coupler having the following formula

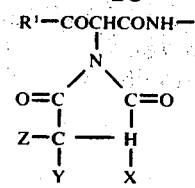

wherein $R_1$ is an aryl group; $R_2$ is an aryl group; X is a hydrogen atom, or an alkyl, acyl, carboxymethyl, alkoxycarbamylmethyl, carbamylmethyl, aryl, aralkyl, nitro or amino group; and Y and Z are individually a hydrogen atom, or an alkyl, ureido, aryl, aralkyl, benzylidene, styryl or anilino group.

* * * * *